United States Patent [19]

Loveless

[11] Patent Number: 5,022,693
[45] Date of Patent: Jun. 11, 1991

[54] OSTOMY BAG HOLDER

[75] Inventor: Kenneth L. Loveless, Spring Hill, Fla.

[73] Assignee: Cornell Research Foundation, Inc., Ithaca, N.Y.

[21] Appl. No.: 450,823

[22] Filed: Dec. 14, 1989

[51] Int. Cl.[5] .................... A61M 27/00; A47K 17/00
[52] U.S. Cl. ..................................... 294/1.1; 604/332; 16/110 R; 16/114 R; 294/165; 294/27.1
[58] Field of Search .................... 248/95, 364, 99, 100; 16/110 R, 114 R, 114 B; 604/343, 345, 332; 294/165, 27.1, 137, 33, 170, 1.1, 1.3, 1.4, 19.1, 27.1; 15/257.1, 257.4, 257.7

[56] References Cited

U.S. PATENT DOCUMENTS

| | | | |
|---|---|---|---|
| 1,526,822 | 2/1925 | Backer | 294/1.1 |
| 2,253,444 | 8/1941 | Muller | 248/75 |
| 2,505,289 | 4/1950 | Haslett | 294/1.1 |
| 2,660,772 | 12/1953 | Ehrhardt | 24/295 |
| 2,923,949 | 2/1960 | Platt | 68/235 D |
| 2,986,789 | 6/1961 | Abraham | 24/507 X |
| 3,847,332 | 11/1974 | Murai | 248/99 |
| 4,012,067 | 3/1977 | Travis | 294/1.4 |
| 4,014,584 | 3/1977 | Bau | 294/1.4 |
| 4,149,745 | 4/1979 | Willis | 294/1.4 |
| 4,159,139 | 6/1979 | Gawedzinski | 15/257.1 |
| 4,323,272 | 4/1982 | Fortier | 294/1.4 |
| 4,395,840 | 8/1983 | Banks, Jr. | 294/19.1 |
| 4,642,106 | 2/1987 | Downey | 604/332 |

OTHER PUBLICATIONS

E-Z Clean advertisement; Summer Issue of "Ostomy Quarterly"; vol. 27, page 36 (1990).

Primary Examiner—Johnny D. Cherry
Assistant Examiner—Cathleen Pringle
Attorney, Agent, or Firm—Jones, Tullar & Cooper

[57] ABSTRACT

An ostomy bag holder has a pair of diverging spring arms which have hooks on their free ends. These arms are joined to a handle which carries a tether line that is provided with a weighted end. The spring arm hooks are engageable with apertured tabs on a mouth rim of an ostomy bag so that the bag can be handled and manipulated during its emptying and cleaning.

8 Claims, 1 Drawing Sheet

U.S. Patent
June 11, 1991
5,022,693
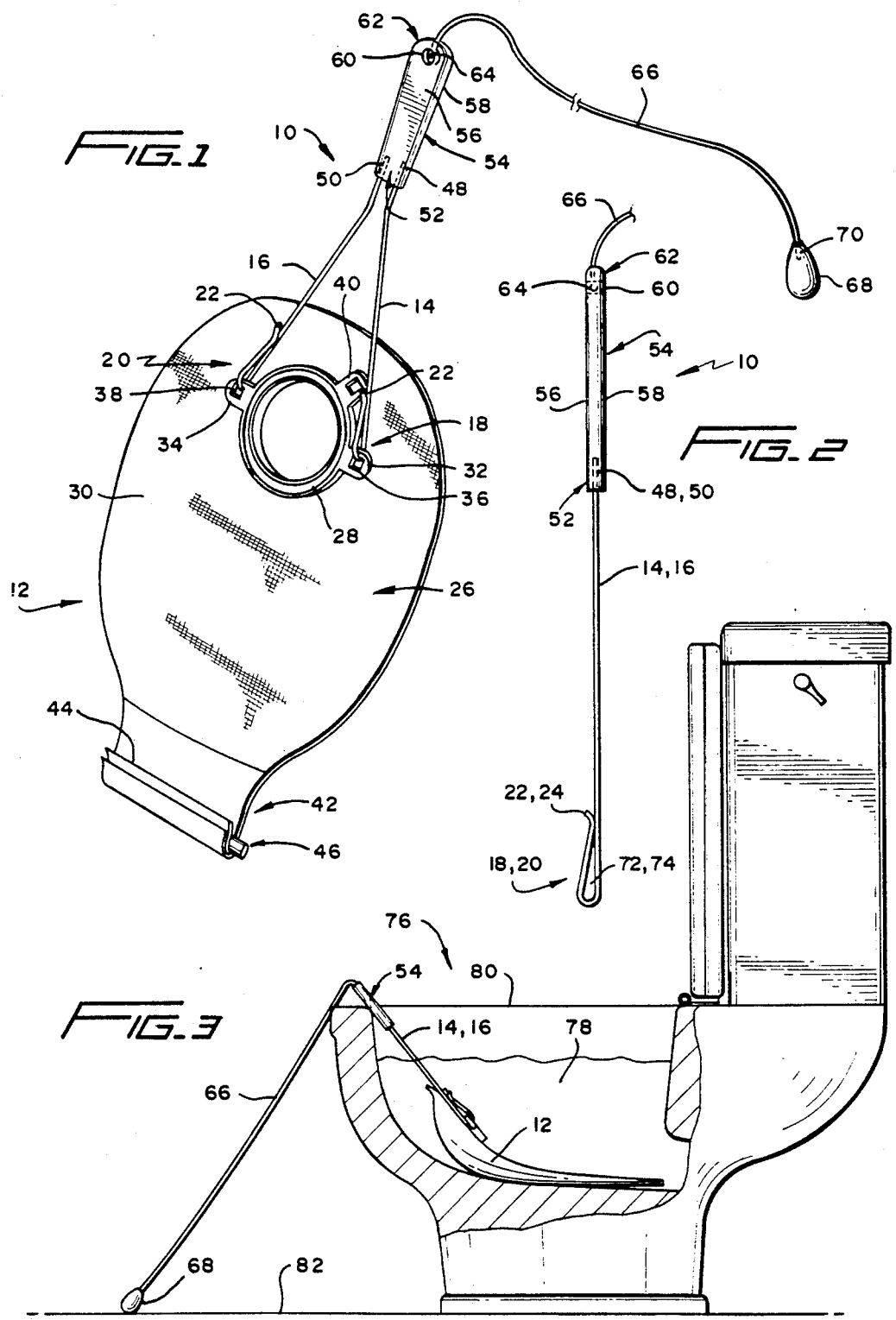

OSTOMY BAG HOLDER

FIELD OF THE INVENTION

The present is directed generally to an ostomy bag holder. More particularly, the present invention is directed to an ostomy bag holder and manipulator. Most specifically, the present invention is directed to an ostomy bag holder and manipulator for a reusable ostomy bag The ostomy bag holder of the present invention is intended for use in the handling and manipulation of a reusable ostomy bag during cleansing of the reusable bag by the ostomate. The ostomy bag holder is structured to allow the ostomate, or a person assisting an ostomate, to easily and adeptly attach the holder to a reusable ostomy bag, to manipulate the bag during emptying, and to retain the bag in a toilet during cleaning of the bag. The ostomy bag holder of the present invention is useable with various types of ostomy bags.

DESCRIPTION OF THE PRIOR ART

In this country, there are approximately 1 million people who have undergone a surgical procedure which is referred to generally as an ostomy. Additionally, approximately 100,000 new ostomy surgeries are performed each year. In surgery of this type, the surgeon brings a portion of the colon, or other body member through a surgically created opening in the abdominal wall. This opening forms a stoma or mouth whose edges are sutured to the person's skin. The stoma that is thus created does not have any sphincter muscle and thus cannot be voluntarily opened and closed by the ostomate. This requires that some type of a pouch be worn by the ostomate to receive bodily discharges and to retain them until the pouch can be removed and cleaned or replaced As with many so-called convenience products, disposable ostomy bags or pouches tend to become expensive when a long-term use is contemplated. Thus the typical ostomate is apt to use an ostomy bag which is intended to be cleaned and reused.

Many ostomates are elderly and their manipulative skills may have lessened with age. Many ostomates, regardless of their age, have some apprehension about coming into contact with bodily waste products, such as feces, and are desirous of being able to handle their ostomy bags or pouches in a manner which will minimize the likelihood of contact with the contents of the pouch. A typical ostomy bag has a raised and resilient mouth rim which snap fits about a flange that has been adhesively attached to the skin of the ostomate surrounding the stoma. It is thus necessary that the mouth rim of the ostomy bag be removed from the flange before the bag can be cleaned. This procedure requires some manipulative skill and may subject the ostomate to contact with the contents of the bag. Once the bag has been removed from the flange, its tail closure is opened and the contents of the pouch are emptied, typically into a toilet, which is then flushed. Once empty, the bag must be thoroughly rinsed and soaked, to be sure that it is completely empty and clean for reuse.

In the past, the typical ostomate has removed the filled pouch by hand and has held the upper end of the pouch, adjacent the mouth rim, with one hand while removing the tail closure with the other hand. These various manipulations are not easy to perform and have resulted in droppage of the still full pouch and possible spillage of the contents. The need to manually grasp the pouch by the ostomate, the possibility of the pouch being dropped, and the possibility of contact with the pouch's contents are all functions of the structure of the pouch and the unavailability of suitable aids.

After the pouch has been emptied, it must be rinsed and cleaned. In the past, this has often been done by using a basin of water because the ostomate may not have been easily able to place the ostomy bag in a toilet bowl to which detergent has been added, and may not be able to hold the bag in the toilet for flushing to rinse the bag and then to remove the bag after it has been cleaned. Additionally, some ostomates may find the idea of 15 putting their hands in a toilet somewhat unpleasant.

The prior art does not appear to have provided a solution to this problem. While various diaper clamps and holders are known generally for use in suspending non-disposable diapers in toilet bowls for cleaning and rinsing, none of these devices are useable with an ostomy bag. A prior art implement for evacuating the contents of a drainable ostomy pouch is shown in U.S. Pat. No. 4,642,106 to Downey. This patent shows an implement which will aid the user in forcing the contents of the pouch out through the tail opening but is not useable to handle, manipulate and hold the ostomy bag during its removal, emptying and cleaning.

As will readily be attested to by the ever increasing numbers of ostomates in this country, there is a need for an ostomy bag holder and manipulating tool which will simplify the daily life of the ostomy bag wearer. Such a device is missing in the prior art and its need is answered by the present invention which is a significant advance in the art.

SUMMARY OF THE INVENTION

It is an object of the present invention to provide an ostomy bag holder.

A further object of the present invention is to provide an ostomy bag holder and manipulator.

Another object of the present invention is to provide an ostomy bag holder and manipulator which is useable with a non-disposable ostomy bag.

Yet a further object of the present invention is to provide an ostomy bag holder which is useable to support and retain an ostomy bag in a toilet during rinsing.

Still another object of the present invention is to provide an ostomy bag holder which has ostomy bag rim engaging arms.

Even yet a further object of the present invention is to provide an ostomy bag holder which has an easily graspable handle.

As will be set forth in detail in the description of the preferred embodiment, which is presented subsequently, the ostomy bag holder in accordance with the present invention includes a pair of diverging arms which are each provided with a recurving hook at their distal ends. These hooks are engageable in apertures in tabs formed on the mouth rim of a generally conventional reusable ostomy pouch. The proximal ends of these arms are secured in an easily graspable handle which allows the ostomate to handle this bag holder without fear of dropping it. An elongated length of an inert plastic line is attached to the opposite end of the handle and carries a weight at its free end. In use, this line is draped over the rim of a toilet bowl and the weight is disposed on the floor. This line and weight thus keeps the handle in place, even if the toilet is flushed, and facilitates retrieval of the bag holder from the toilet once cleaning and rinsing of the bag has been completed.

The ostomy bag holder in accordance with the present invention allows the ostomate to handle his ostomy bag during removal and cleaning with much greater confidence and security than was possible in the past. The two diverging arms are preferably formed of spring wire and their distal ends can be moved closer or further apart to accommodate various sized ostomy bag mouth rims. Each arm ends in a recurving hook that is engageable with an aperture in a tab that is formed in the bag's mouth rim. This securely holds the bag and allows the ostomate to more easily detach the bag from the stoma surrounding flange.

After the bag has been separated from the flange, it will be supported by the bag holder of the present invention during opening of the bag's tail clamp and emptying of the bag's contents into a toilet. This may be accomplished by placing the bag and holder in the toilet bowl, after removing the clip, and by gently shaking the bag to remove the feces. Bag handling is made easier and there is little likelihood that the bag will be dropped After the contents of the bag have been emptied into a toilet, the bag and bag holder may be removed from the toilet and the toilet may be flushed. The bag and handle may then be again placed in the toilet together with a suitable detergent for a short soaking period. Once this soaking is complete, the bag and holder are again removed from the toilet which is again flushed. The bag and holder may again be placed in the toilet again for rinsing. By placing the flexible line over the rim of the toilet bowl, and by placing the weight on the end of the line on the floor, the bag holder is maintained in a generally upright and easily graspable orientation. Additionally, the weight and line will assist in holding the bag holder and bag in the toilet if the toilet is flushed during cleaning or rinsing of the ostomy bag. Once the bag has been rinsed, it can be removed from the toilet by using the bag holder of the present invention. Subsequent to this, the now cleaned bag may be detached from the bag holder and dried. Alternatively, the bag and holder may be dried together by using the handle of the holder to suspend the bag and holder from a suitable hook.

The ostomy bag holder and manipulating device of the present invention is specifically structured for use with ostomy bags. It will not harm or puncture the bags and allows the ostomate, or one assisting in the care of an ostomate, to quickly and adeptly handle an ostomy bag during emptying, rinsing and cleaning. As will be apparent, it is far superior to manual handling of the ostomy bag and represents a substantial improvement over the prior art.

BRIEF DESCRIPTION OF THE DRAWINGS

While the novel features of the ostomy bag holder of the present invention are set forth with particularity in the appended claims, a full and complete understanding of the invention may be had by referring to the detailed description of the preferred embodiment which is set forth subsequently, and as illustrated in the accompanying drawings, in which:

FIG. 1 is a perspective view of the ostomy bag holder of the present invention and depicting the holder in use with an ostomy bag;

FIG. 2 is a side elevation view of the ostomy bag holder of the present invention; and FIG. 3 is a side elevation view, partly in section, and showing the ostomy bag holder of the present invention in use with an ostomy bag that has been placed in a toilet.

DESCRIPTION OF THE PREFERRED EMBODIMENT

Referring initially to FIG. 1, there may be seen generally at 10 a preferred embodiment of an ostomy bag holder in accordance with the present invention. Ostomy bag holder 10 is depicted in FIG. 1 in use with an ostomy bag, generally at 12. Ostomy bags, such as the bag 12 are generally well known in the art and are commercially available from several manufacturers. The ostomy bag depicted at 12 in FIG. 1 is made by E.R. Squibb & Sons, Inc. and is sold under the name ConvaTec ®. While this particular ostomy bag is depicted and discussed in the present application, it will be understood that ostomy bags are made by several manufacturers and that the ostomy bag holder 10 of the present invention is equally useable with these various ostomy bags. It will further be understood that the ostomy bag holder 10 of the present invention is useable with various ostomy bags, such as those useable in a colostomy, urostomy, or other similar procedures which have resulted in a stoma that requires a receptor bag or other container.

As may be seen in FIG. 1, ostomy bag holder, generally at 10 has a pair of spaced, generally diverging arms 14 and 16. In the preferred embodiment, these arms 14 and 16 are formed of stainless steel spring wire having a diameter of generally about 1/16 of an inch. Each arm 14 and 16 is generally about 4 to 6 inches long with 5 inches being the preferred length. The arms diverge from each other at an angle of divergence which may be varied in accordance with the diameter of the ostomy bag mouth rim, as will be discussed shortly. Each arm 14 and 16 has a first, distal end which is formed into a recurving hook, as seen generally at 18 and 20, respectively. As is shown most clearly in FIG. 2, each hook 18, 20 has a rounded end 22, 24 that is directed somewhat outwardly out of the plane defined by the two arms 14 and 16. These outwardly directed hook ends 22 and 24 facilitate engagement of the hooks 18 and 20 with an ostomy bag.

As may be seen in FIG. 1, ostomy bag 12 has a flexible body 26 that is formed of any suitable inert flexible material. A bag mouth rim 28 is joined to a front wall 30 of ostomy bag 12. This mouth rim 28 includes a pair of peripherally spaced belt engageable tabs 32 and 34. These belt engageable tabs 32 and 34 have apertures 36 and 38 which, as is generally well known in the art, are useable to allow a belt to be attached to the ostomy bag to assist in holding the bag in place on a stoma flange, not shown. The ostomy bag mouth rim 28 is also conventionally provided with a grip tab 40 which is useable by the ostomate, or a person caring for him, in the removal and attachment of the ostomy bag 12. Ostomy bag 12 further typically has a tail portion 42 which terminates in a discharge opening 44 that is closeable by a removable clip assembly 46. This bag structure and clip assembly, as discussed above, are commercially available products which are not part of the present invention.

Spring wire arms 14 and 16, as may be seen in FIGS. 1 and 2 terminate in second, proximal ends 48 and 50 which are embedded or otherwise securely received in a first end 52 of a plastic handle, generally at 54. This handle has opposed, front and back grasping surfaces 56 and 58 which could be flat or which could be provided with suitable grip enhancing surface ridges, projections or the like, not shown. Further, the overall shape of handle 54 could be altered to provide a more easily grasped and held handle, if desired. An aperture 60 is provided at a second end 62 of handle 54. This aperture may have any suitable shape. In the preferred embodiment, handle 54 is formed from any one of a number of nylon or other inert plastic materials.

A first end 64 of an elongated flexible tether line 66 is attached to handle 54 generally in the area of handle aperture 60. Any suitable means may be used to secure first end 64 of tether line 66 to handle 54. A suitable weight, 68, such as a 1 oz. lead weight, is secured to a second end 70 of tether line 66. In the preferred embodiment, weight 68 is attached to tether line 66 and then is dip coated with a suitable hardenable plastic composition which insures that weight 68 will not come unattached from line 66. This tether line 66 may be made from any suitable inert nylon or other plastic and, in the preferred embodiment, has a diameter of generally about 0.050 inch.

In use, the ostomate, or a person responsible for the care of the ostomate, will slide the spring arms 14 and 16 down between the person's adhesively attached stoma flange and the front wall 30 of the ostomy bag 12. The spring arms 14 and 16 can be suitably adjusted so that the spacing of their free ends 18 and 20 will correspond to the diameter of the mouth rim 28. This is easily done by bending the arms inwardly or outwardly to vary their angle of divergence. The rounded ends 22 and 24 of the recurve hooks 18 and 20 will engage the belt tab apertures 36 and 38 in the belt tabs 32 and 34 as the ostomy holder 10 is pulled gently upwardly. Once so engaged, the ostomy holder 10 may be again pulled slightly upwardly to place the recurve hooks 18 and 20 on the distal ends of the spring arms 14 and 16 securely in the belt tab apertures 36 and 38. Since these spaced diverging arms 14 and 16 are made of spring wire, the hook ends 22 and 24 will separate from the arms 14 and 16 as the tabs pass by, and will then return to their original position thereby retaining the apertured belt tabs 32 and 34 of the ostomy bag mouth rim 28 in the loops 72 and 74 that are defined by the recurving hooks 18 and 20. Once these hooks 18 and 20 have been so engaged, the bag mouth rim 28 may be separated from its associated stoma flange, not shown, by application of an appropriate outward pulling force applied to handle 54, possibly in conjunction with a corresponding force applied to bag grip tab 40. It will be understood that any ostomy belt which may have been attached to belt tabs 32 and 34 will have been removed.

If the ostomate himself is removing his own bag 12, he may do so while standing adjacent a toilet. If such is the case, he can remove ostomy bag clip 46 from the tail 42 of the ostomy bag 12 and hold the tail 42 closed until he has removed the bag 12 from the stoma flange and has placed the bag tail 42 adjacent the open toilet. If a person aiding the ostomate has removed the bag 12, he or she will then move to a toilet or other disposal container before removing the tail clip 46. In either case, the contents of the bag 12 may then be emptied into the toilet while holding the bag 12 by the handle 54 of the ostomy bag holder 10. A gentle shaking action may aid in the emptying the bag. Once the bag's contents have been discharged into the toilet they are disposed of by flushing the toilet.

The empty bag 12 may now be placed in a toilet 76 as seen in FIG. 3. The bag 12 itself will be placed in the water 78 in toilet 76 with arms 14 and 16 extending out of the water. The handle 10 of ostomy bag holder 54 may be placed against a rim portion 80 of toilet 76 and the tether line 66 will be deployed outside of the toilet with weight 68 resting on the floor 82. The bag 12 and holder 10 may be left in the toilet bowl while a detergent solution is added. Gentle agitation of handle 54 will be sufficient to thoroughly rinse out and clean ostomy bag 12. After this has been accomplished, the bag 12 may be temporarily elevated above the toilet by raising handle 54, or may be left in toilet 76, while the toilet is flushed to remove the detergent solution. The bag 12 and holder 10 may then again be rinsed in toilet 76 or may alternatively be rinsed in a basin of water. Once this rinsing has been accomplished, the cleaned ostomy bag may be detached from holder 10 and hung up to dry. Alternatively, the cleaned ostomy bag and holder 10 may be hung up to dry together by suspending the handle 54 of holder 10 on a suitable hook or the like (not shown) which will be received in aperture 60 in handle 54. Even if the handle 54 of the ostomy bag holder 10 should slip down into the water 78 in toilet 76, the tether line 66 and weight 68 will remain outside the toilet for easy grasping.

The ostomy bag holder 10 in accordance with the present invention is a significant aid to the person with an ostomy and greatly reduces the time required to empty and clean ostomy bags 12. Further, the ostomy bag holder 10 is much more easily grasped and manipulated than is the small grip tab 40 on the mouth rim 28 of the bag 12. Similarly, once the belt tabs 32 and 34 have been received in the hook loops 72 and 74, the ostomy bag is quite securely attached to the ostomy bag holder 10. Particularly in situations where the ostomate may not be as manually dexterous as he once was, the easily grasped handle 54 of the bag holder 10 affords a much better grip than is provided by grip tab 40. At the same time, the ostomy bag holder 10 allows the person servicing the bag 12 to do so without contacting the possibly soiled mouth rim 28. This is particularly beneficial where the ostomate may be unable to care for himself. As will be readily apparent, the ostomy bag of the present invention provides a level of convenience and user satisfaction which is far superior to the prior art.

While a preferred embodiment of the ostomy bag holder in accordance with the present invention has been set forth with specificity hereinabove, it will be apparent to one of skill in the art that a number of changes in, for example, the overall size of the holder, the length of the tether line, the size and shape of the weight and the like could be made without departing from the true spirit and scope of the present invention which is accordingly to be limited only by the following claims.

What is claimed is:

1. An ostomy bag holder which is usable to hold and to manipulate an ostomy bag which has a mouth rim with spaced apertured tabs, said ostomy bag holder comprising:
   a handle having first and second spaced ends;
   first and second spaced arms each having first and second ends, said first ends of said first and second spaced arms being secured to said first end of said handle;
   means at said end of each of said first and second spaced arms to engage an apertured tab of a mouth rim of an ostomy bag; and an elongated tether line secured at a first end to said second end of said ostomy bag holder handle and extendable away from said second end of said handle.

2. The ostomy bag holder of claim 1 wherein said first ends of said first and second spaced arms are spaced from each other at a first distance which is less than a second distance at which said second ends of said spaced arms are spaced from each other.

3. The ostomy bag holder of claim 1 wherein said means to engage an apertured tab of a mouth rim of an ostomy bag is a hook on said second end of each of said first and second arms.

4. The ostomy bag holder of claim 3 wherein said hook at said second end of each of said spaced first and second arms is a recurve hook having an outwardly extending free end.

5. The ostomy bag holder of claim 1 wherein said handle has opposed front and back grasping surfaces.

6. The ostomy bag holder of claim 1 wherein said second end of said handle includes an aperture and further wherein said first end of said tether line is secured to said handle at said aperture.

7. The ostomy bag holder of claim 1 wherein a weight is attached to a second end of said tether line.

8. The ostomy bag holder of claim 1 wherein said first and second arms are formed from spring wire.

* * * * *